(12) United States Patent
Morone et al.

(10) Patent No.: US 11,466,161 B2
(45) Date of Patent: Oct. 11, 2022

(54) BENZOYL-COUMARIN POLYMERIZABLE PHOTOINITIATORS

(71) Applicant: IGM RESINS ITALIA S.R.L., Milan (IT)

(72) Inventors: Marika Morone, Lipomo County (IT); Vincenzo Razzano, Siena SI (IT); Stephen Postle, Glen Rock, NJ (US); Gabriele Norcini, Comabbio (IT)

(73) Assignee: IGM RESINS ITALIA S.R.L., Milan (IT)

( * ) Notice: Subject to any disclaimer, the term of this patent is extended or adjusted under 35 U.S.C. 154(b) by 297 days.

(21) Appl. No.: 16/771,412

(22) PCT Filed: Dec. 6, 2018

(86) PCT No.: PCT/IB2018/059702
§ 371 (c)(1),
(2) Date: Jun. 10, 2020

(87) PCT Pub. No.: WO2019/116176
PCT Pub. Date: Jun. 20, 2019

(65) Prior Publication Data
US 2020/0347235 A1    Nov. 5, 2020

Related U.S. Application Data

(60) Provisional application No. 62/597,069, filed on Dec. 11, 2017.

(51) Int. Cl.
| C09D 4/00 | (2006.01) |
| C07D 311/16 | (2006.01) |
| C08F 122/20 | (2006.01) |
| C09D 11/101 | (2014.01) |
| C09D 11/107 | (2014.01) |
| C09D 11/30 | (2014.01) |
| C09D 11/02 | (2014.01) |
| C09D 135/02 | (2006.01) |

(52) U.S. Cl.
CPC ............ *C09D 4/00* (2013.01); *C07D 311/16* (2013.01); *C08F 122/20* (2013.01); *C09D 11/101* (2013.01); *C09D 11/107* (2013.01); *C09D 11/30* (2013.01); *C09D 135/02* (2013.01)

(58) Field of Classification Search
CPC . C07D 311/16; C08F 2/48; C08F 2/50; C08F 122/20; C09D 11/101; C09D 11/107; C09D 11/30; C09D 11/38; C09D 4/00; C09D 135/02
See application file for complete search history.

(56) References Cited

U.S. PATENT DOCUMENTS

| 5,385,808 A * | 1/1995 | Tokoh | C08L 83/10 430/283.1 |
| 6,201,087 B1 * | 3/2001 | Herr | C08F 220/302 526/263 |
| 2005/0270441 A1 * | 12/2005 | Chari | G02F 1/1334 349/86 |
| 2007/0179266 A1 * | 8/2007 | Studer | C09K 19/3852 526/341 |

FOREIGN PATENT DOCUMENTS

| KR | 20090108154 | 10/2009 |
| WO | 2005/014677 | 2/2005 |
| WO | 2010/133381 | 11/2010 |
| WO | 2014018826 | 1/2014 |
| WO | 2017/216699 | 12/2017 |

OTHER PUBLICATIONS

International Search Report by the EPO dated Feb. 20, 2019 for PCT/IB2018/059702.

* cited by examiner

*Primary Examiner* — Anh T Vo
(74) *Attorney, Agent, or Firm* — Silvia Salvadori

(57) ABSTRACT

The present invention relates to a series of novel polymerizable compounds based on 3-ketocoumarins, which are useful as photoinitiators and sensitizers, to compositions comprising said compounds and to a process for photopolymerizing comprising them.

Formula (I)

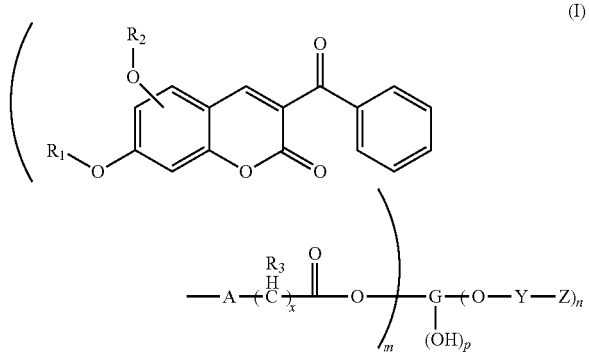

16 Claims, No Drawings

BENZOYL-COUMARIN POLYMERIZABLE PHOTOINITIATORS

This application is a U.S. national stage of PCT/IB2018/059702 filed on 6 Dec. 2018, which claims priority to and the benefit of U.S. Provisional Application No. 62/597,069 filed 11 Dec. 2017, the contents of which are incorporated herein by reference in their entireties.

TECHNICAL FIELD

The present invention relates to a series of novel polymerizable compounds based on 3-ketocoumarins, which are useful as photoinitiators and sensitizers, to compositions comprising said compounds and to a process for photopolymerizing comprising them.

TECHNICAL BACKGROUND

Photoinitiators used in radiation curable coatings need to have good cure speed, in particular good surface curing, low odor, good solubility and low yellowing.

Among the light radiation sources used in this field, light emitting diodes (LED), a semiconductor light source, have been the subject of significant development over the past few years because of the advantages of low temperature operation and extremely long life in comparison with conventional medium pressure mercury arc curing lamps. LED lamps are advantageous because of the inherently small size of LED units, their longer lifetime, their robustness and their ability to be easily engineered, for example into commercial printing systems.

When using LED lamps to photocure inks and coatings, it is necessary to use selected photoinitiator systems that are tuned to the wavelength of this light source. While Mercury arc lamps typically have a polychromatic emission spectrum, emitting light in all regions of the UV-visible spectrum from 200 to 450 nm, LED lamps usually have only a single emission band in the range 365-420 nm.

Photoinitiators, absorbing in the region between 365 nm and 420 nm, are thus required to make full use of the recent development of LEDs with increasing power. Moreover, since high concentration of photoactive substance are usually required for LED applications, the photoinitiators should have a high compatibility with the photopolymerizable system. Thioxanthones, such as isopropyl thioxanthone (ITX) and its derivatives, and acyl phosphine oxides are photoinitiators commonly used in this field.

Unfortunately, the thioxanthone derivatives commonly used both as photoinitiators and sensitizers are prone to yellowing upon exposure, thereby forming degradation products with limited stability. As a result, the original yellowing can shift unpredictably upon storage. Especially in imaging, e.g. inkjet printing, this unstable yellowing behavior makes quite difficult the control of the image tone in the final image.

Acyl phosphine oxides initiators, on the other hand, result in medium volatile aldehyde type of degradation products, producing a background smell of the cured coatings or the printed.

Moreover when radiation curable compositions are used for food packaging, toys or dental applications, the amount of residues or degradation products of photoinitiators able to diffuse out of the cured coating into the surrounding medium (migration) it's a critical issue. Low molecular weight compounds are usually not completely built into the polymer network and are prone to be extracted or to diffuse out of the cured composition. Therefore, there is a need and a continuous effort to design photoinitiators having a reduced tendency to migrate out or to be extracted of the cured composition.

One approach to overcome these problems is to use photoinitiators which contain an ethylenically unsaturated moiety; for example, WO2005014677 (Ciba) and KR20090108154 (LG Chemical Ltd.) describe derivatives of 3-ketocoumarins with a (meth)acrylated function. The ethylenically unsaturated group enables the photoinitiator to be incorporated into the polymeric structure, during the curing process. Unfortunately, the claimed compounds do not show the necessary reactivity at LED wavelength.

An alternative approach is to use photoinitiators of increased molecular size, which have an increased probability to be blocked into the cured products, resulting in reduced levels of migratable and/or extractable degradation products.

This solution is disclosed in PCT/US2013/052184 (Sun Chemical Corporation). However, these photoinitiators have a strong tendency to lose reactivity. Hence, often considerable amounts of these photoinitiators are required in order to reach the desired curing speed, thereby also increasing the viscosity to an undesirable level for a great number of applications of radiation curable compositions, such as e.g. inkjet printing. Moreover above a concentration of 10-12% non-acrylate functional materials either start to behave as plasticizers or just reduce the crosslink density of the cured film to a point where its mechanical properties are impaired.

That means that there continues to be a demand for other photoinitiators having improved interactions with radiation-curable coating systems.

SUMMARY OF THE INVENTION

We have now discovered a series of novel polymerizable compounds based on 3-ketocoumarins which have good solubility, high reactivity, low yellowing and give cured products which have extremely low odor and a very low tendency to migrate and/or to be extracted.

It is known to those skilled in the art that, for a photoinitiator to be suitable to initiate crosslinking of acrylate and/or methacrylate monomers and oligomers, the photoinitiator and/or the radicals produced by photolysis under ultraviolet light must have some mobility and be able to diffuse to be able to initiate polymerization of said acrylate and methacrylate monomers and oligomers. Thus, photoinitiators of larger molecular weight and size are known to be slower in reactivity than related smaller molecules. While this is a disadvantage, there may be compensating features concerning the larger molecular weight photoinitiators, such as the lack of migration of the photoinitiator to diffuse out of a coated assembly comprising the photoinitiator and/or its photolysis products. Surprisingly, we have discovered that the new polymerizable ketocoumarins demonstrate comparable reactivity to the smaller ketocoumarin photoinitiator molecules previously described.
(we have moved the above in the experimental section)

DESCRIPTION OF THE INVENTION

The present invention relates to a new class of polymerizable photoinitiators, especially suitable for food compliant radiation curable compositions and methods for preparing said photoinitiators.

The compounds of the present invention comprise a polymeric core based on polyhydroxy/polyalcoxy polymeric compound, which is chemically bonded to one or more groups derived from 3-ketocoumarins and containing at least an ethylenically unsaturated bond.

According to one of its aspects, an object of the present invention is a polymerizable photoinitiator of Formula (I):

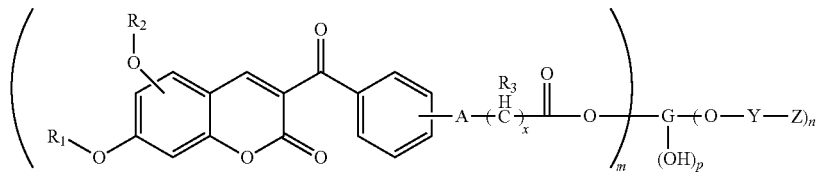

wherein

G is a residue of an optionally alkoxylated polyhydroxy compound;

m, n and p are numbers and m+n+p has a value ranging from 2 to 10;

m and n are independently a number ranging from 1 to 8;

p is has a value ranging from 0 to 8;

x is an integer number with a value ranging from 0 to 10, and when x is 0 A is directly linked to the carbonyl group;

A represents, each independently, $CHR_3$, O, S, $NR_4$ where $R_4$ is an alkyl $C_1$-$C_6$ group;

Y represents, each independently a direct bond or a substituted or unsubstituted divalent linking group comprising 1 to 14 carbon atoms;

Z represents, each independently, a radically polymerizable functional group selected from the group consisting of an acrylate, a methacrylate, a styrene, an acryl amide, a maleate, a fumarate, an itaconate, a vinyl ether, an allyl ether, an allyl ester, a maleimide, a vinyl nitrile and a vinyl ester;

$R_3$ represents, each independently hydrogen, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

$R_1$, $R_2$ are, each independently, hydrogen, alkyl $C_1$-$C_{12}$, substituted or unsubstituted phenyl, substituted or unsubstituted aryl, substituted or unsubstituted heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy.

DETAILED DESCRIPTION OF THE INVENTION

According to the present invention:

In various embodiments, in Formula (I) m+n+p is has a value ranging from 2 to 8, and in some embodiments has a value ranging from 3 to 6.

In various embodiments, in Formula (I), m is has a value ranging from 1 to 6 and in some embodiments has a value ranging from 1 to 4.

In various embodiments, in Formula (I), n is has a value ranging from 1 to 6 and in some embodiments has a value ranging from 1 to 4.

When p is different from 0, the compounds of Formula (I) have free alcoholic groups.

In various embodiments, in Formula (I) A is $CHR_3$, O, or A is $CHR_3$.

In various embodiments, in Formula (I) x has a value ranging from 0 to 6, more preferably x is 1 to 4.

In advantageous embodiments in Formula (I), Y is a direct bond, a divalent linking group in this case Y is an optionally substituted alkylene group, an aliphatic ether containing group, more preferably when Y is a divalent linking group is —(—$CH_2$—$CH_2$—O—)$_k$—$CH_2$—$CH_2$—, —(—$CH_2$—)$_k$— with k being an integer equal to 1, 2, 3, 4, 5 or 6.

In Formula (I) Y may advantageously be a direct bond.

In various embodiments, in Formula (I) Z is an acrylate group, a methacrylate group, or may advantageously be an acrylate group.

In Formula (I) of the present disclosure:

G is the residue of an optionally alcoxylated polyhydroxy compound, which can be selected from monomeric, oligomeric and polymeric polyols, and mixture thereof.

Examples of suitable monomeric and oligomeric polyols are glycerol, di-glycerol, tri-glycerol, triethanolamine, trimethylol propane, di-trimethylol propane, pentaerythritol, di-pentaeritrithol, sugar alcohols, such as sorbitol, mannitol and xylitol, mixtures thereof.

Examples of polymeric polyols are alkoxylated compounds, polyhydroxy polyethers, which can be both aliphatic or aromatic, polyhydroxy polyesters, polyhydroxy polyamides, polyhydroxy polyimides, polyhydroxy polycarbonates; styrene-allyl alcohols copolymers.

The alkoxylated compounds are particularly preferred for the realization of the present invention. Examples of such alkoxylated compounds are monomeric and oligomeric polyols mentioned above, which have been alkoxylated, for example ethoxylated and/or propoxylated and/or butoxylated. Other suitable examples are linear or branched polyamines, which have been alkoxylated, and polyalkoxylated diamines, such as ethoxylated ethylene diamine and ethoxylated 1,3-propylene diamine. In the alkoxylated compounds of the invention, each group reactive toward the alkylene oxide can bring from 0 to 15 alkoxy units, preferably from 1 to 6 alkoxy units.

In various embodiments G is chosen among monomeric and oligomeric polyols.

In various other embodiments G is chosen among monomeric and oligomeric polyols which have been ethoxylated and/or propoxylated.

In various embodiments, G has a number average molecular weight not greater than 1500, more preferably not greater than 800, and most preferably not greater than 500.

In various embodiments, G is chosen among glycerol, ethoxylated and/or propoxylated glycerol, di-glycerol, ethoxylated and/or propoxylated di-glycerol, trimethylolpropane, ethoxylated and/or propoxylated trimethylolpropane, di-tri methylolpropane, ethoxylated and/or propoxylated di-trimethylolpropane, penthaerythritol, ethoxylated and/or propoxylated penthaerythritol, di-penthaerythritol, ethoxylated and/or propoxylated di-penthaerythritol, sorbitol, ethoxylated and/or propoxylated sorbitol, triethanolamine, ethoxylated and/or propoxylated triethanolamine.

In various embodiments $R_1$, $R_2$ are each independently an alkyl $C_1$-$C_{12}$ group, and may advantageously be an alkyl $C_1$-$C_4$ group.

In the present text the expressions "alkyl" or "alkyl group" mean, where not differently indicated, a linear or branched alkyl chain containing from 1 to 12 carbon atoms and includes all possible variants for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl etc.

The expressions "cycloalkyl" or "cycloalkyl group" mean, where not differently indicated, an aliphatic ring containing from 5 to 6 carbon atoms which can be cyclopentyl, cyclohexyl.

The expressions "aryl" or "aryl group" mean for example substituted or unsubstituted phenyl group, substituted or unsubstituted naphthyl group, anthracenyl group, indenyl group, fluorenyl group and others.

The expressions "heteroaryl" or "heteroaryl group" mean for example furan, thiophene, pyrrole, oxazole, isooxazole, thiazole, isothiazole, imidazole, pyrazole, pyrane, pyridine, pyrrolidine, piperidine, indole, quinoline, isoquinoline, xanthene, carbazole, acridine, indoline, julolidine and others.

The term substituted means that a group bears a substituent that can be halogen atom, an alkyl, cycloalkyl, alkoxy, alkylamino, dialkylamino, alkylthio or arylthio group, heterocyclic groups, more specifically, methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, methoxy, ethoxy, propoxy, isopropoxy, butoxy, pentyloxy, phenoxy, hydroxyl, acetoxy, —$PO_3H$, methylthio, ethylthio, i-propylthio, n-propylthio, phenylthio, mercapto, acetylthio, thiocyano, methylsulfinyl, methylsulfonyl, dimethylsulfonyl, sulfonate groups, fluorine atom, chlorine atom, bromine atom, iodine atom, trimethylsilyl, triethylsilyl, trimethylstannyl, furyl, thienyl, pyridyl, piperidino, morpholino, pyrrolidyl groups and so on.

According to various embodiments, $R_1$ and $R_2$ are the same $C_1$-$C_4$ alkyl, advantageously methyl.

According to a various embodiments, $OR_2$ is in 5-position.

According to a various embodiments, A is in 4-position (para-position respect to the carbonyl group).

According to various embodiments, $R_3$ is hydrogen.

The compounds represented by Formula (I) can be prepared according to conventional methods known to the expert in the art. For example, by a multistep reaction as follows

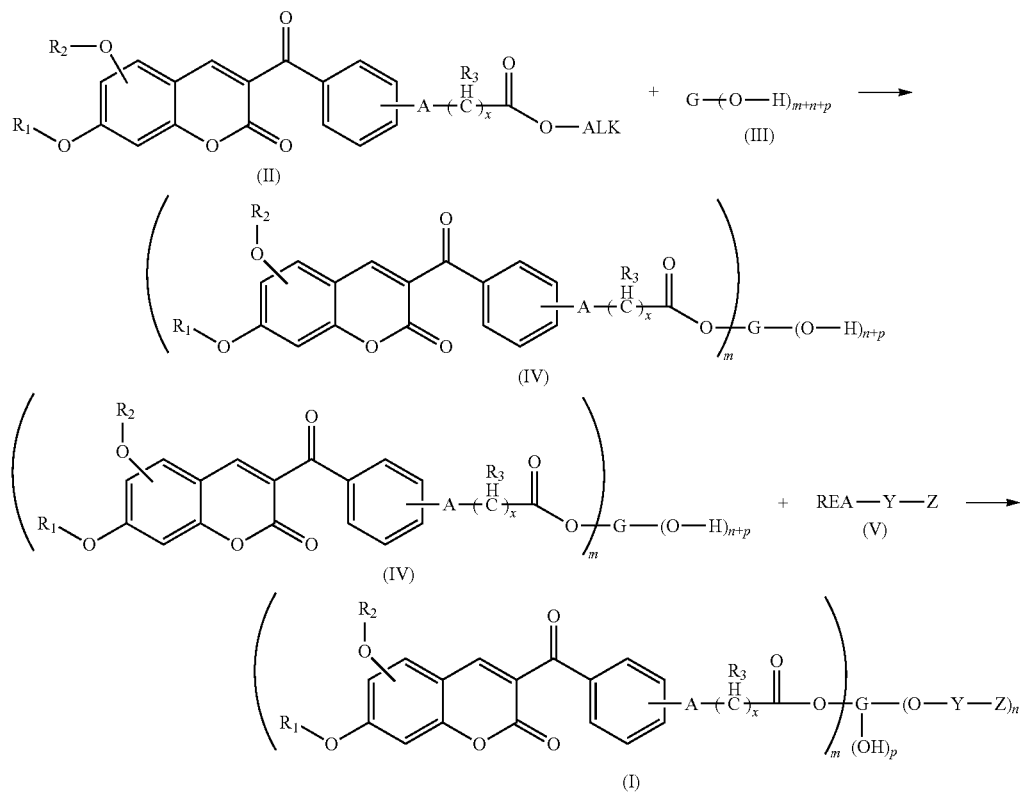

wherein ALK is an alkyl group, for example methyl or ethyl, G is as described above and REA is a reactive group like Cl or $CH_2$=CH—.

The compounds of Formula (II) and (III) can be prepared according to known procedures.

More details relating to the synthesis of representative compounds of the invention are reported in the Experimental Section of the present description.

The process for the preparation of compounds of Formula (I) described above is a further subject-matter of the invention. Other synthesis routes can anyway be used.

The compounds of Formula (I) are useful as photoinitiators. The use of the compounds of Formula (I) as photoinitiators in photopolymerization processes is a further subject-matter of the present invention, as well as a method for light curing which comprises using the compounds of Formula (I) as photoinitiators.

For "photoinitiator" it is hereby meant a molecule that possesses a functional group able to generate radicals (alone or in combination with a co-initiator) capable of starting a polymerization by exposure to light with an appropriate wavelength.

Compounds of Formula (I) are useful, in particular, in photopolymerizable compositions suitable for inks, coatings and three dimensional objects (so-called "three-dimensional printing) that can be photopolymerized by exposure to a radiation source.

For their use, compounds of Formula (I) are included in photopolymerizable compositions which comprise at least one ethylenically unsaturated compound and at least one compound of Formula (I).

By "ethylenically unsaturated" compound we mean a monomer, oligomer, prepolymer having at least one unsaturated double bond, or a mixture thereof, capable of undergoing radical polymerization. Also monomers, oligomers and prepolymers combinations with different degrees of unsaturation can be used.

The monomers suitable for the realization of the present invention are those commonly used in the field and can be chosen, for example, among vinyl ethers, N-vinyl pyrrolidone, N-vinyl caprolactam, mono- and poly-functional allyl ethers such as trimethylol propane diallyl ether, styrenes and alpha-methyl styrenes, esters of (meth)acrylic acid with aliphatic alcohol, glycols, polyhydroxylated compounds such as pentaerythritol or trimethylol propane, esters of vinyl alcohol with acrylic or aliphatic acid, derivatives of fumaric and maleic acids.

Suitable oligomers or prepolymers for the present invention comprise, for example, polyesters, polyacrylates, polyurethanes, epoxy resins, polyethers with acrylic, maleic or fumaric functionalities.

Monomers, oligomers and prepolymers, which are commonly used in photopolymerizable ink are preferred. These compounds are well known to the expert in the art and are described for example in WO2014/063997.

The photocurable compositions of the present invention preferably comprise from 50 to 99.9% by weight, of at least one ethylenically unsaturated compound and from 0.1 to 35% by weight of a compound of Formula (I).

More preferably, the photocurable compositions of the present invention comprise from 70 to 98.9% by weight, of at least one ethylenically unsaturated compound and from 0.1 to 20% by weight of a compound of Formula (I), more preferably from 0.2 to 15% by weight.

Using the expression "by weight", we mean that the value are expressed as percentage weight with respect to the total composition weight.

Besides the above-mentioned compounds, other components normally used in the field and known to the experts in the art can be added to the photopolymerizable compositions of the invention. For example, thermal stabilizers, photo-oxidation stabilizers, anti-oxidants, fillers, dispersants, coloring and/or opacifying substances and other additives of general use. Others components of the photopolymerizable compositions of the invention can be non-photopolymerizable polymers present as chemically inert substances, as an example nitrocellulose, polyacrylic esters, polyolefins, etc.

The photopolymerizable compositions of the invention can also conveniently include a co-initiator, which is a molecule that acts as hydrogen donor that increases the polymerization rate. The co-initiators are known in the art and they are typically alcohols, thiols, amines or ethers that have an available hydrogen bonded to a carbon adjacent to the heteroatom. Such co-initiators are generally present in an amount from 0.2 to 15% by weight, preferably from 0.2 to 8% by weight. Suitable co-initiators include, but are not limited to aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cicloexyl amine, benzyldimethyl amine, di-cyclohexyl amine, N-phenyl glycine, triethyl amine, phenyl-diethanol amine, triethanolamine, piperidine, piperazine, morpholine, pyridine, quinoline, esters of dimethylamino benzoic acid, Michler's ketone (4,4'-bis-dimethyl aminobenzophenone) and corresponding derivatives.

As the amine co-initiator, an amine-modified acrylate compound can be used, examples of such amine-modified acrylate include acrylates modified by reaction with a primary or secondary amine that are described in U.S. Pat. No. 3,844,916, EP 280222, U.S. Pat. Nos. 5,482,649, 5,734,002 or US2013/0012611.

Preferred co-initiators are Esacure A198 (bis-N,N-[4-dimethylaminobenzoyl) oxyethylen-1-yl]-methylamine), Esacure EDB (ethyl-4-dimethylamino benzoate) and Photomer 4250 all commercialized by IGM Resins B.V., 2-ethylhexyl-4-dimethylaminobenzoate and N-phenyl glycine.

The photopolymerizable compositions of the invention can also conveniently include other photoinitiators commonly used in the field.

Other photoinitiators, co-initiators and further components that may be comprised in the composition of the invention are described for example in the document WO2014/063997 mentioned above.

According to an advantageous aspect of the invention the compounds of Formula (I) are used as sentitizers of sensitizable photoinitiators in photopolymerizable compositions.

For "sensitizer" or "sensitizer agent" it is hereby meant a molecule that, by an energy transfer process, activates a photoinitiator at a wavelength at which the photoinitiator alone would not be reactive.

In this case, the photopolymerizable composition may comprise from 70 to 98.9% by weight of at least one photopolymerizable compound, from 0.1 to 10% by weight of at least one compound of Formula (I), as sensitizer and from 1 to a 15% by weight of at least one sensitizable photoinitiator, for example a ketosulfone or an α-aminoketone and, optionally, from 0.2 to 8% by weight of a co-initiator.

The preferred sensitizable photoinitiator are 1-[4-[(4-benzoyl-phenyl)-thio]-phenyl]-2-methyl,2-[(4-methyl-phenyl)-sulfonyl]-propan-1-one (Esacure 1001, from IGM Resins B.V.), 2-methyl-1-(4-methylthiophenyl)-2-morpholinopropane-1-one), 2-benzyl-2-dimethylamino-1-(4-morpholinophenyl)-butan-1-one, and (2-(dimethylamino)-2-[(4-methylphenyl)methyl]-1-[4-(4-morpholinyl)phenyl]-1-butanone).

The compounds of Formula (I) work both in transparent photopolymerizable compositions and in non-transparent or colored compositions and, in particular, are useful for the preparation of photopolymerizable inks. The photoinitiators and the compositions of the invention are particularly suited for the preparation of photopolymerizable inks for ink-jet printing.

For this reason, the photopolymerizable composition of the invention can further comprise from 0.01 to 30% by weight of colorants.

Colorants which can be used in the photopolymerizable inks of the invention are dyes, pigments or a combination thereof. Organic and/or inorganic pigments may be used. The colorants are preferably pigments or polymeric dyes, most preferably pigments. The pigments may be black, white, cyan, magenta, yellow, red, orange, violet, blue, green, brown, mixtures thereof, and the like, as well as other conventional pigments, well known to the skilled in the art.

Exemplary organic pigments include insoluble azo pigments, condensed azo pigments, azo lake, and chelate azo pigments; polycyclic pigments, such as phthalocyanine pigments, perylene and perinone pigments, anthraquinone pigments, quinacridone pigments, dioxane pigments, thioindigo pigments, isoindolinone pigments, and quinophthalone pigments; dye chelates, such as basic dye chelates and acid dye chelates; dye lakes, such as basic dye lakes and acid dye lakes; and nitro pigments, nitroso pigments, aniline black, and fluorescent pigments.

For photopolymerizable white inks, the white colorants are preferably present in an amount of 3% to 30% by weight of the ink composition, and more preferably 5% to 25%. Usually the other colorants are present in the photopolymerizable inks of the invention in the range of 0.01 to 10% by weight, preferably in the range of 0.1 to 5% by weight.

Colorants for ink-jet printing are particularly preferred.

In addition to the main components, the photopolymerizable inks can contain also other specific ingredients such as co-initiators and other photoinitiators, such as those described in the preceding paragraphs and in the same amount, dispersants, surfactants and other additives which are well known to the expert in the art. Said components are described for example in WO2014/063997.

The compositions and the inks described above are also subject-matter of the present invention.

According to another of its aspects, it is a further subject-matter of the invention a process for photocuring photopolymerizable compositions and inks, which process comprises:

I) preparing a photopolymerizable composition comprising:
 a) from 50 to 99.9% by weight, preferably from 70 to 98.9% by weight, of at least one ethylenically unsaturated compound;
 b) from 0.1 to 35% by weight, preferably from 0.1 to 20% by weight, and more preferably from 0.2 to 15% by weight of at least one compound of Formula (I), as defined above;

II) photopolymerizing the composition of step I with a light source

Accordingly, a large number of the most varied kinds of light source may be used, the light source emits at wavelengths comprised from approximately 200 nm to approximately 600 nm. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams, X-rays and lasers. The distance between the lamp and the substrate according to the invention to be exposed may vary according to the intended use and the type and strength of the lamp and may be, for example, from 1 cm to 150 cm.

In various embodiments, the light is an ultraviolet light or blue light.

Particularly preferred are LED light source emitting at wavelengths from 365 nm to 420 nm, preferably 365 nm, 385 nm and 395 nm.

Optionally, said photopolymerizable composition may be applied to a substrate prior to carrying out the photopolymerization step with said light source. Examples of substrates include but are not limited to polyethylene, polypropylene, polyester terephthalate, nylon, paper, board, wood, metal and glass, and other substrates well known to those skilled in the art. Examples of application processes include but are not limited to printing by flexography, gravure, screen, ink jet, lithography, or intaglio, coating by spray, airless spray, rollcoat, flexography, gravure, curtain, cascade, slot, brush and wire-wound roller. Other methods of applying said photopolymerizable composition will be apparent to those skilled in the art.

Said photopolymerizable composition may also be applied over a substrate already comprising a coated or printed layer. Said photopolymerizable composition may, after photopolymerization with said light source, be overprinted or overcoated with one or more compositions suitable for printing or coating.

The article obtained by applying said photopolymerizable composition to said substrate by said means of coating or printing, and photopolymerizing by said light source, with or without further elaboration of the article by further coating or printing, is a further subject-matter of this invention.

According to a preferred embodiment, in the photopolymerizing process, the compound of Formula (I) is defined as in the preferred embodiments above disclosed.

As it will be demonstrated in the Experimental section, surprisingly, we found that compounds of Formula (I) showed a reactivity superior to the compound described in WO2005014677, example A2 when used in the same weight amount, with mercury lamp and LED lamps both in clear and pigmented systems. Moreover, compounds of Formula (I) are almost as reactive as their parent single molecules (i.e. not polymerized) while all polymerizable compounds described in literature always show a reduction of reactivity ranging from 30 to 50%, as it will be seen in the examples.

also, it has been observed that the compounds of Formula (I) overcome the drawbacks of the prior art, as they show an absorbance region between 365 and 420 nm (and therefore can be used as photoinitiators by LED lamps), do not provoke yellowing, have a good photochemical reactivity and solubility do not generate bad smelling degradation product and are safe for health and environment.

EXPERIMENTAL SECTION

Examples

Example 1

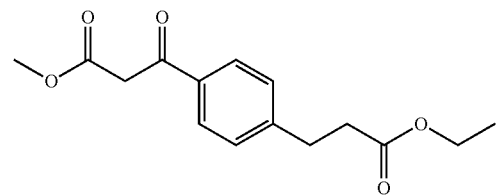 [SMILES: CCOC(=O)CCc1ccc(C(=O)CC(=O)OC)cc1]

Under nitrogen atmosphere 67.0 g (502.5 mmoles) of aluminum chloride were added in small portions under stirring at 0° C. to a solution of 30.0 g (168.3 mmoles) of ethyl 3-phenylpropionate and 24.0 g (175.8 mmoles) of methyl 3-chloro-3-oxopropionate in 250 mL of dichloromethane. After stirring at room temperature for 4 hours, the reaction was poured in ice and water and the resulting mixture was kept under stirring for 30 minutes. Then the organic phase was separated, washed with water, dried over sodium sulfate, filtered and the solvent removed by distillation under vacuum obtaining 37.7 g of a yellow oil (yield 80%).

$^1$H-NMR (CDCl$_3$, δ ppm): 1.22 (t, 3H), 2.65 (t, 2H), 3.05 (t, 2H), 3.75 (s, 3H), 3.98 (s, 2H), 4.10 (q, 2H), 7.30 (d, 2H), 7.85 (d, 2H).

Example 2

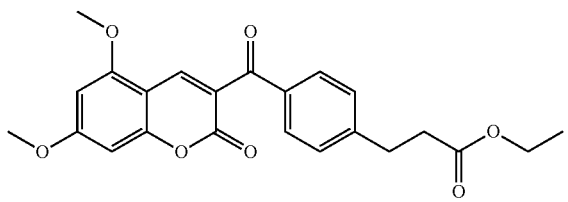 [SMILES: CCOC(=O)CCc1ccc(C(=O)c2cc3c(OC)cc(OC)cc3oc2=O)cc1]

34.1 g (122.5 mmoles) of Example 1 and 0.86 g (10.1 mmoles) of piperidine were added to a solution of 22.3 g (122.4 mmoles) of 4.6-dimethoxy-2-hydroxy-benzaldehyde in 100 mL of ethanol. The mixture was stirred for 2 hours under reflux, then cooled to room temperature. The reaction product was recovered by filtration obtaining 25.0 g of a white-yellow solids (yield 50%).

$^1$H-NMR (CDCl$_3$, δ ppm): 1.23 (t, 3H), 2.65 (t, 2H), 3.10 (t, 2H), 3.89 (m, 6H), 4.12 (q, 2H), 6.30 (d, 1H), 6.45 (d, 1H), 7.30 (d, 2H), 7.79 (d, 2H), 8.40 (s, 1H).

Example 3

Wherein a+b+c is about 8.5

3.05 g (14.61 mmoles) of butyltin hydroxide oxide hydrate were added in small portions under stirring at 150° C. to a mixture of 6.00 g (14.62 mmoles) of Example 2 and 5.55 g (hydroxyl n° 370/g) of Rolfor GL/609 (ethoxylated glycerol, Lamberti S.p.A.). The mixture was stirred at 150° C. for 8 hours eliminating ethanol by distillation. After cooling to room temperature, the reaction mixture was dissolved in dichloromethane and filtered. The filtrate was washed with water, dried over sodium sulfate and the solvent removed by distillation under vacuum obtaining 10.74 g of a yellow-brown oil (yield 99%). The product was used directly in the next step.

0.43 g (4.75 mmoles) of acryloyl chloride were added dropwise under stirring at 0° C. in nitrogen atmosphere to a solution of 1.20 g of the compound prepared in the previous step and 0.50 g (4.95 mmoles) of triethylamine in 30 mL of dichloromethane. After stirring at room temperature for 2 hours, the reaction was complete and 1M sodium hydrogen carbonate aqueous solution was added. The organic phase was separated, washed with water, dried over sodium sulfate and the solvent removed by distillation under vacuum. The crude product was purified by flash column chromatography on silica gel (dichloromethane:methanol 95:5) obtaining 1.00 g of a yellow-brown oil (yield 75%).

$^1$H-NMR (CDCl$_3$, δ ppm): 2.65 (m, 10H), 3.00 (m, 10H), 3.50-3.75 (m, 128H), 3.90 (s, 30H), 4.20 (m, 10H), 4.30 (m, 10H), 5.82 (d, 5H), 6.15 (m, 5H), 6.30 (s, 5H), 6.40 (d, 5H), 6.45 (s, 5H), 7.30 (d, 10H), 7.75 (d, 10H), 8.4 (m, 5H).

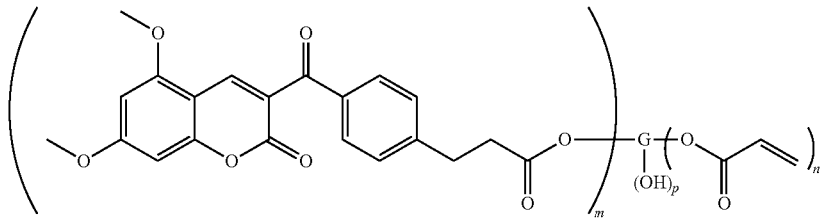

m = 1.2, p = 0.6, n = 1.2

G =

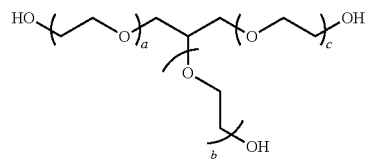

Example 4

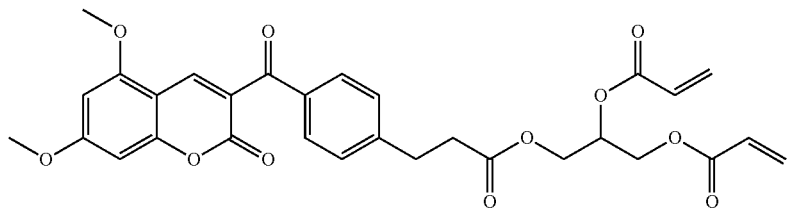 [SMILES: C=CC(=O)OCC(COC(=O)CCc1ccc(C(=O)c2cc3c(OC)cc(OC)cc3oc2=O)cc1)OC(=O)C=C]

2.54 g (12.16 mmoles) of butyltin hydroxide oxide hydrate were added in small portions under stirring at 150° C. to a mixture of 5.00 g (12.18 mmoles) of Example 2 and 30.00 g (325.73 mmoles) of glycerol. The mixture was stirred at 150° C. for 28 hours eliminating ethanol by distillation. After cooling to room temperature, the reaction mixture was suspended in 200 mL of dichloromethane/water (1:1) and kept under stirring for 1 hour. Then the organic phase was separated, dried over sodium sulfate and the solvent removed by distillation under vacuum. The crude product was purified by flash column chromatography on silica gel (ethyl acetate) obtaining 3.35 g of an off-white solid (yield 60%). The product was used directly in the next step.

0.83 g (9.17 mmoles) of acryloyl chloride were added dropwise under stirring at 0° C. in nitrogen atmosphere to a solution of 2.00 g (4.38 mmoles) of the compounds prepared in the previous step and 0.95 g (9.39 mmoles) of triethylamine in 30 mL of dichloromethane. After stirring at room temperature for 1 hour, the reaction was complete and water was added. The organic phase was separated, dried over sodium sulfate and the solvent removed by distillation under vacuum. The crude product was purified by flash column chromatography on silica gel (ethyl acetate) obtaining 0.95 g of a yellow oil (yield 38%).

$^1$H-NMR (CDCl$_3$, δ ppm): 2.69 (t, 2H), 3.00 (t, 2H), 3.90 (m, 6H), 4.22-4.29 (m, 2H), 4.33-4.38 (m, 2H), 5.35 (m, 1H), 5.85 (m, 2H), 6.09 (dd, 1H), 6.12 (dd, 1H), 6.30 (d, 1H), 6.39 (dd, 1H), 6.43 (dd, 1H), 6.45 (d, 1H), 7.30 (d, 2H), 7.78 (d, 2H), 8.40 (s, 1H).

Example 5

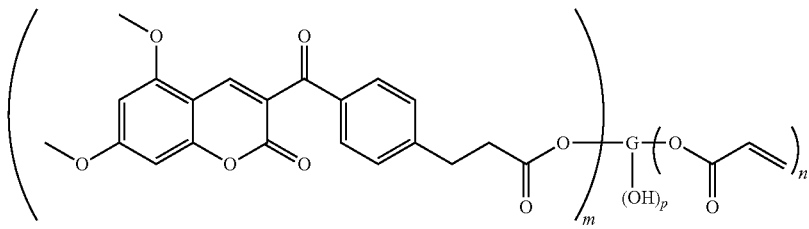

m = 2.0, p = 0.7, n = 1.3
G =

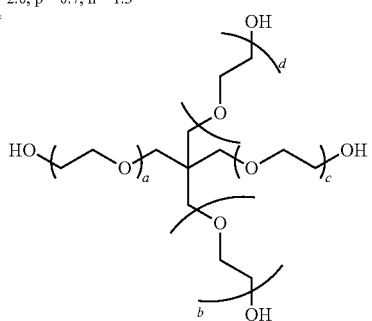

Wherein a+b+c+d is about 5

0.51 g (2.44 mmoles) of butyltin hydroxide oxide hydrate were added in small portions under stirring at 150° C. to a mixture of 2.00 g (4.87 mmoles) of Example 2 and 0.85 g (hydroxyl n° 642/g) of Polyol 4640 (ethoxylated pentaeritritol, Perstorp Specialty Chemicals A.B.). The mixture was stirred at 150° C. for 8 hours eliminating ethanol by distillation. After cooling to room temperature, the reaction mixture was dissolved in dichloromethane and filtered. The filtrate was washed with water, dried over sodium sulfate and the solvent removed by distillation under vacuum obtaining 2.40 g of a yellow-brown oil (yield 91%). The product was used directly in the next step.

1.24 g (13.70 mmoles) of acryloyl chloride were added dropwise under stirring at 0° C. in nitrogen atmosphere to a solution of 2.40 g of the compound prepared in the previous step and 1.46 g (14.46 mmoles) of triethylamine in 80 mL of dichloromethane. After stirring at room temperature for 2 hours, the reaction was complete and 1M sodium hydrogen carbonate aqueous solution was added. The organic phase was separated, washed with water, dried over sodium sulfate and the solvent removed by distillation under vacuum. The crude product was purified by flash column chromatography on silica gel (dichloromethane:methanol 95:5) obtaining 2.50 g of a yellow-brown oil (yield 95%).

$^1$H-NMR (CDCl$_3$, δ ppm): 2.65 (m, 12H), 3.00 (m, 12H), 3.35-3.75 (m, 50H), 3.90 (m, 36H), 4.10-4.30 (m, 20H), 5.80 (m, 4H), 6.10 (m, 4H), 6.30 (s, 6H), 6.35 (m, 4H), 6.45 (m, 6H), 7.30 (m, 12H), 7.75 (m, 12H), 8.40 (m, 6H).

Example 6

Wherein a+b+c+d+e+f is about 21

0.51 g (2.44 mmoles) of butyltin hydroxide oxide hydrate were added in small portions under stirring at 150° C. to a mixture of 2.00 g (4.87 mmoles) of Example 2 and 1.36 g (hydroxyl n° 300/g) of Sorbilene RE/20 (ethoxylated sorbitol, Lamberti S.p.A.). The mixture was stirred at 150° C. for 8 hours eliminating ethanol by distillation. After cooling to room temperature, the reaction mixture was dissolved in dichloromethane and filtered. The filtrate was washed with water, dried over sodium sulfate and the solvent removed by distillation under vacuum obtaining 3.10 g of a yellow-brown oil (yield 99%). The product was used directly in the next step.

0.51 g (5.63 mmoles) of acryloyl chloride were added dropwise under stirring at 0° C. in nitrogen atmosphere to a solution of 3.10 g of the compound prepared in the previous step and 0.59 g (5.84 mmoles) of triethylamine in 60 mL of dichloromethane. After stirring at room temperature for 2 hours, the reaction was complete and 1M sodium hydrogen carbonate aqueous solution was added. The organic phase was separated, washed with water, dried over sodium sulfate and the solvent removed by distillation under vacuum. The crude product was purified by flash column chromatography on silica gel (dichloromethane:methanol 95:5) obtaining 1.26 g of a yellow-brown oil (yield 39%).

$^1$H-NMR (CDCl$_3$, δ ppm): 2.65 (m, 14H), 3.00 (m, 14H), 3.50-3.80 (m, 170H), 3.90 (m, 42H), 4.20 (m, 14H), 4.30 (m, 6H), 5.80 (d, 3H), 6.10 (m, 3H), 6.30 (s, 7H), 6.35-6.45 (m, 10H), 7.30 (d, 14H), 7.75 (m, 14H), 8.40 (m, 7H).

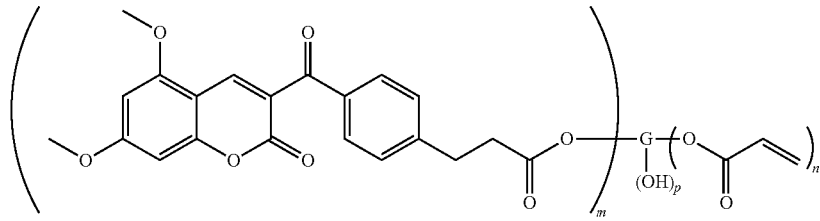

m = 4.0, p = 0.3, n = 1.7

G =

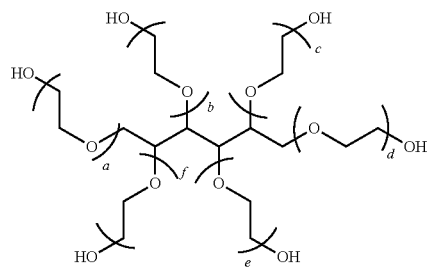

Example 7

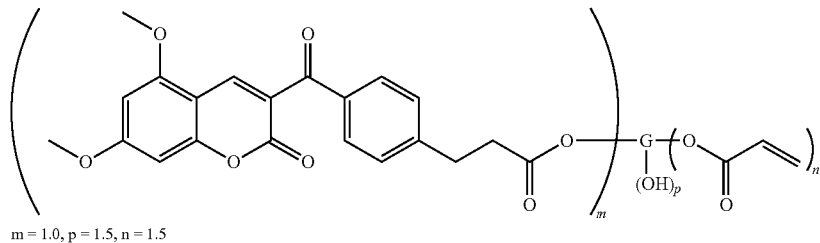

m = 1.0, p = 1.5, n = 1.5

G =

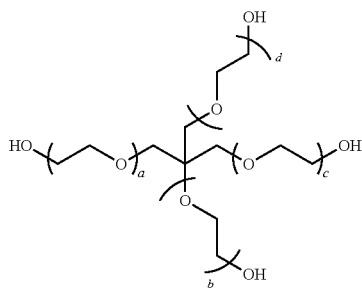

Wherein a+b+c+d is about 5

0.51 g (2.44 mmoles) of butyltin hydroxide oxide hydrate were added in small portions under stirring at 150° C. to a mixture of 2.00 g (4.87 mmoles) of Example 2 and 1.70 g (hydroxyl n° 642/g) of Polyol 4640 (ethoxylated pentaeritritol, Perstorp Specialty Chemicals A.B.). The mixture was stirred at 150° C. for 8 hours eliminating ethanol by distillation. After cooling to room temperature, the reaction mixture was dissolved in dichloromethane and filtered. The filtrate was washed with water, dried over sodium sulfate and the solvent removed by distillation under vacuum obtaining 3.00 g of a yellow-brown oil (yield 86%). The product was used directly in the next step.

2.10 g (23.20 mmoles) of acryloyl chloride were added dropwise under stirring at 0° C. in nitrogen atmosphere to a solution of 2.70 g of the compound prepared in the previous step and 2.46 g (24.36 mmoles) of triethylamine in 80 mL of dichloromethane. After stirring at room temperature for 2 hours, the reaction was complete and 1M sodium hydrogen carbonate aqueous solution was added. The organic phase was separated, washed with water, dried over sodium sulfate and the solvent removed by distillation under vacuum. The crude product was purified by flash column chromatography on silica gel (dichloromethane:methanol 95:5) obtaining 2.20 g of a yellow-brown oil (yield 66%).

$^1$H-NMR (CDCl$_3$, δ ppm): 2.65 (m, 8H), 3.00 (m, 8H), 3.35-3.75 (m, 46H), 3.90 (m, 24H), 4.10-4.30 (m, 20H), 5.80 (d, 6H), 6.10 (m, 6H), 6.30 (m, 4H), 6.35-6.45 (m, 10H), 7.30 (m, 8H), 7.75 (m, 8H), 8.40 (m, 4H).

Example 8

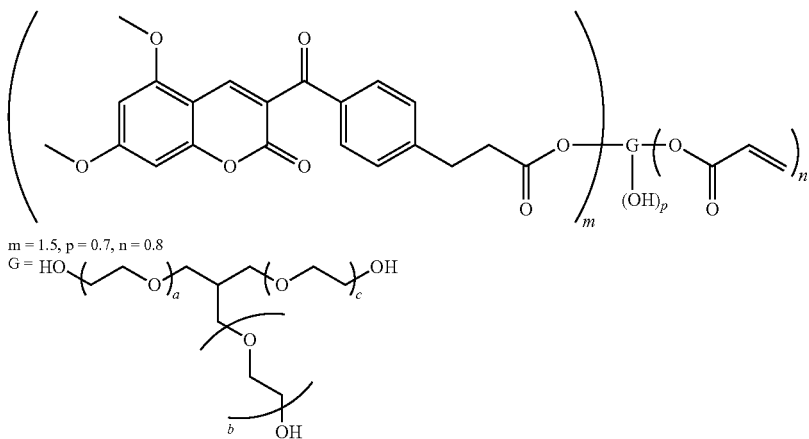

m = 1.5, p = 0.7, n = 0.8

Wherein a+b+c is about 1

1.36 g (6.51 mmoles) of butyltin hydroxide oxide hydrate were added in small portions under stirring at 100° C. to a mixture of 2.00 g (4.87 mmoles) of Example 2 and 0.91 g (3.25 mmoles) of triethanolamine ethoxylate 1 EO/OH (purchased from Sigma Aldrich) in 5 mL of p-xylene. The mixture was stirred for 8 hours under reflux eliminating ethanol by distillation. After cooling to room temperature, the reaction mixture was diluted with dichloromethane and filtered. The filtrate was washed with 1M sodium hydrogen carbonate aqueous solution and then with water. The organic phase was dried over sodium sulfate and the solvent removed by distillation under vacuum obtaining 2.50 g of a yellow-brown oil (yield 93%). The product was used directly in the next step.

1.10 g (12.15 mmoles) of acryloyl chloride were added dropwise under stirring at 0° C. in nitrogen atmosphere to a solution of 2.5 g of the compound prepared in the previous step and 1.29 g (12.77 mmoles) of triethylamine in 80 mL of dichloromethane. After stirring at room temperature for 2 hours, the reaction was complete and 1M sodium hydrogen carbonate aqueous solution was added. The organic phase was separated, washed with water, dried over sodium sulfate and the solvent removed by distillation under vacuum. The crude product was purified by flash column chromatography on silica gel (dichloromethane:methanol 95:5) obtaining 2.50 g of a yellow-brown oil (yield 91%).

$^1$H-NMR (CDCl$_3$, δ ppm): 2.60-3.05 (m, 14H), 3.43-3.71 (m, 12H), 3.90 (s, 12H), 4.09-4.32 (m, 6H), 5.8 (m, 1H), 6.02-6.19 (m, 1H), 6.30 (m, 2H), 6.31-6.40 (m, 1H), 6.45 (m, 2H), 7.30 (m, 4H), 7.78 (m, 4H), 8.40 (m, 2H)

Example 9

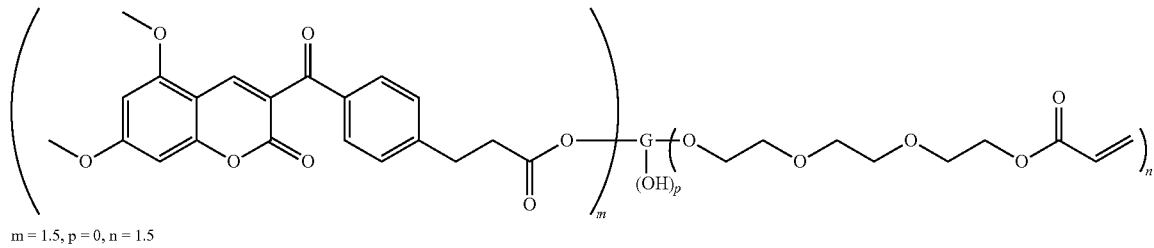

m = 1.5, p = 0, n = 1.5

G =

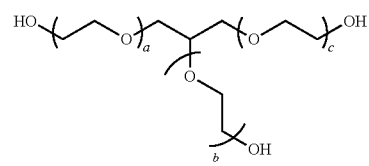

3.05 g (14.61 mmoles) of butyltin hydroxide oxide hydrate were added in small portions under stirring at 150° C. to a mixture of 6.00 g (14.62 mmoles) of Example 2 and 5.55 g (hydroxyl n° 370/g) of Rolfor GL/609 (ethoxylated glycerol, Lamberti S.p.A.). The mixture was stirred at 150° C. for 8 hours eliminating ethanol by distillation. After cooling to room temperature, the reaction mixture was dissolved in dichloromethane and filtered. The filtrate was washed with water, dried over sodium sulfate and the solvent removed by distillation under vacuum obtaining 10.74 g of a yellow-brown oil (yield 99%). The product was used directly in the next step.

3.50 g of the compound prepared in the previous step were added to a mixture of 3.42 g (18.37 mmoles) 2-(vinyloxyethoxy)ethyl acrylate and 3.5 mL of ethyl acetate. 0.030 g (0.136 mmoles) of BHT and 0.016 g (0.140 mmoles) of trifluoroacetic acid were added and the mixture was heated to 70° C. The reaction was allowed to continue for 8 hours at 70° C. Activation of the ion exchanger: 25 g of Lewatit™ M600 MB was treated with 75 mL of 1N sodium hydroxide aqueous solution and stirred for 2 hours. The ion exchanger was isolated by filtration, washed several times with water and dried until constant weight. The reaction mixture was allowed to cool down to room temperature and 0.40 g of the actived ion exchanger were added. The mixture was stirred for 1 hour at room temperature. The ion exchanger was removed by filtration and the ethyl acetate was removed under reduced pressure obtaining 6.90 g of a yellow-brown oil (yield 100%).

Example 10

Comparative Tests

The 3-ketocoumarins of the invention, were compared with Omnipol 3TX (Acrylic acid 2-[2-(1-{2-{1-[2-(2-acryloyloxy-ethoxy)-ethoxy]-ethoxymethyl}-3-(1-{2-[2-(1-methyleneallyloxy)-ethoxy]-ethoxy}-ethoxy)-2-[2-(9-oxo-9Hthioxanthen-2-yloxy)-acetylamino]-propoxy}-ethoxy)-ethoxy]-ethyl ester diluted in 50% 2-(2-vinyloxyethoxy) ethyl acrylate, IGM Resins B.V.) (COMP-1) and the 3-ketocoumarins of the prior art prepared as described in WO2005014677 Example A2 (COMP-2).

Example 10.1

Reactivity Test

Example 10.1.1

Clear Formulation

The photopolymerizable compositions for the test were prepared dissolving the photoinitiators and the co-initiator, Esacure EDB (IGM Resins B.V.), at a concentration of 3% by weight (wt) each in a mixture 99.5:0.5 wt of Ebecryl 605 and Ebecryl 350 (Allnex).

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°. (Table 1)

2) A Mercury lamp (160 W) located at a distance of 65 mm from the sample and at an angle of 30°. (Table 2)

IR spectra were acquired at constant time intervals during the photopolymerization and the reduction over the time of the area of the peaks at 1408 and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 1 and the results with the Mercury lamp are reported in Table 2.

TABLE 1

| Example | 0.5 sec | 2 sec |
| --- | --- | --- |
| Example 3 | 59 | 70 |
| Example 5 | 54 | 58 |
| Example 6 | 61 | 64 |
| Example 7 | 57 | 60 |
| Example 8 | 51 | 56 |
| Example 9 | 45 | 48 |
| COMP-1 | 46 | 50 |
| COMP-2 | 48 | 51 |

TABLE 2

| Example | 0.2 sec | 1 sec |
| --- | --- | --- |
| Example 3 | 55 | 62 |
| Example 5 | 58 | 66 |
| Example 6 | 61 | 69 |
| Example 7 | 54 | 64 |
| Example 8 | 56 | 66 |
| Example 9 | 49 | 56 |
| COMP-1 | 20 | 38 |
| COMP-2 | 61 | 69 |

Example 10.1.2

Cyan Inkjet Ink

The photopolymerizable compositions for the test were prepared by dissolving the photoinitiators and the co-initiator Esacure EDB at a concentration of 5.0% wt each in a cyan ink for ink-jet printing.

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°. (Table 3)
2) A Mercury lamp (160 W) located at a distance of 65 mm from the sample and at an angle of 30°. (Table 4)

IR spectra were acquired at constant time intervals during the photopolymerization and the reduction over the time of the area of the peaks at 1408 cm$^{-1}$ and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 3 and the results with the Mercury lamp are reported in Table 4.

TABLE 3

| Example | 0.5 sec | 2 sec |
| --- | --- | --- |
| Example 3 | 56 | 67 |
| Example 5 | 56 | 68 |

TABLE 3-continued

| Example | 0.5 sec | 2 sec |
| --- | --- | --- |
| Example 6 | 57 | 72 |
| Example 7 | 53 | 69 |
| Example 8 | 52 | 67 |
| Example 9 | 44 | 56 |
| COMP-1 | 30 | 53 |
| COMP-2 | 14 | 33 |

TABLE 4

| Example | 1 sec | 6 sec |
| --- | --- | --- |
| Example 3 | 44 | 75 |
| Example 5 | 39 | 83 |
| Example 6 | 36 | 72 |
| Example 7 | 21 | 57 |
| Example 8 | 34 | 82 |
| Example 9 | 44 | 77 |
| COMP-1 | 3 | 13 |
| COMP-2 | 7 | 21 |

These tests confirm that compounds of Formula (I) are more reactive than the comparatives (COMP-1 and COMP-2).

Example 10.1.3

Reactivity Tests Polymerizable Compounds Versus Single Molecules

The photopolymerizable compositions were prepared as reported in the examples 10.1.1. and 10.1.2.

Then they were placed in the sample lodgment of a FT-IR (FT-IR 430-Jasco), were exposed to a LED source (400 nm) located at a distance of 25 mm from the sample and at an angle of 30°. (Table 5).

IR spectra were acquired at constant time intervals during the photopolymerization and the reduction over the time of the area of the peaks at 1408 cm$^{-1}$ and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 5.

As reference compounds were used Omnipol 3TX (IGM Resins B.V.) (COMP-1), Omnirad ITX (2-isopropyl thioxanthone, IGM Resins B.V.) (COMP-3) and a 3-ketocoumarin of the prior art prepared as described in EP2909243 Example 10 (COMP-4)

TABLE 5

| Example | Clear formulation LED lamp (400 nm) 0.5 s | Cyan Inkjet Ink LED lamp (400 nm) 0.5 s |
| --- | --- | --- |
| Example 6 | 61 | 57 |
| COMP-1 | 46 | 30 |
| COMP-3 | 71 | 58 |
| COMP-4 | 69 | 60 |

From the results above is clear that the new polymerizable ketocoumarin of Example 6 is almost reactive as the reference compound (COMP-4) in fact the reactivity is reduced only of 12% in clear system and of 5% in pigmented system. This is completely unexpected because in literature are always described strong reduction of reactivity when acrylated moieties are present on photoinitiator structures, as example we compared Omnirad ITX (COMP-3) with Omnipol 3TX (COMP-1) (acrylated version of Omnirad ITX) and from Table 5 we can estimated a reduction of reactivity of the 35% in clear system and of the 48% in pigmented system, that is from tree times to almost ten times the reduction observed for the polymerizable compound of Example 6.

Example 10.1.4

Extractability Test

The radiation curable compositions (INV-1, INV-2 and INV-3) were prepared according to Table 6. The weight % (wt %) was based on the total weight of the radiation curable composition.

TABLE 6

|  | INV-1 | INV-2 | INV-3 |
|---|---|---|---|
| Example 3 | 0.5 | — |  |
| Example 9 | — | 1.0 | 1.0 |
| Omnipol ASA | 0.5 | 0.5 |  |
| Photomer 4600 | 1.0 | 1.0 |  |
| VEEA | 4.0 | 3.5 |  |
| Photomer 280 | 0.03 | 0.03 | 0.05 |
| Photomer 4250 |  |  | 0.75 |
| Photomer 4149 |  |  | 2.50 |
| Photomer 4017 |  |  | 2.69 |
| Photomer 4226 |  |  | 3.00 |
| Esacure KIP160 |  |  | 0.150 |
| Omnirad 127 |  |  | 0.250 |

VEEA = 2-(2-Vinyloxyethoxy)ethyl acrylate (from Nippon Shokubai Co, Ltd)
Photomers are from IGM Resins BV The radiation curable composition INV-1, INV-2 and INV-3 were coated on a PE substrate using a bar coater and a 10 μm wired bar. Each coated sample was cured using a Fusion DRSE-120 Q/QNL, equipped with an Hg lamp (240 W) and with a Phoseon equipped with an LED lamp 395 nm (16 W/cm$^2$). The curing speed is shown in Table 7.

TABLE 7

|  | Curing Speed Hg lamp (240 W) m/min | Curing Speed LED lamp 395 nm (16 W/cm$^2$) m/min |
|---|---|---|
| INV-1 | 25 | 10 (2pass) |
| INV-2 | 35 | 10 |
| INV-3 | 35 | 10 |

The samples of 7.068 cm$^2$ of INV-1, INV-2 and INV-3 were put into a 50 ml beaker and extracted with 4.5 ml acetonitrile, using ultrasound for 30 minutes. The extract was transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.45 μm filter. 10 μl of each sample was injected on the HPLC.

The concentration was determined in comparison with a reference sample of a known concentration of the initiator, eluted under the same conditions as the extracted samples.

A total coating weight of 10 g/m$^2$ was assumed for each sample.

In the HPLC trace no residue of Example 3 and Example 9 was detectable. This illustrates that polymerizable photoinitiators according to a preferred embodiment of the present invention are completely built in to the network.

The above experiments show that contrary to what it is disclosed hitherto in the literature, wherein polymerizable photoinitiators provided a significant reduction of the activity compared to the correspondent non-polymerized ketocoumarins, (see for instance the reduction of the activity for the thioxanthone Omnipol 3TX (IGM Resins BV) (MW 946.07 g/mol) compared to Omnirad ITX (IGM Resins BV) (MW 254.3 g/mol) which amounts to 48% in pigmented system under an LED lamp (400 nm)) the polymerizable ketocoumarins of Example 6 above (MW>1000 Da) show a reduction of only 5% in the same conditions (see Example 10.1.3 above).

The multifunctional nature of the photoinitiators of the invention keeps the functionality per gram relatively high and the relatively small core molecular weight renders the material highly soluble in photocurable compositions, especially in photocurable coating compositions.

Moreover, the presence of at least one ethylenically unsaturated group guarantees that the new compounds are copolymerized with the other monomer(s) of the photocurable composition, preventing them from migrating and/or being extracted.

The invention claimed is:
1. A compound of Formula (I)

$$\left( R_1-O \underset{R_2-O}{\overset{}{\diagup}} \text{coumarin-phenyl} \right)_m \text{-A-}(CR_3H)_x\text{-C(O)-O-}\left[ G(OH)_p(O-Y-Z)_n \right]$$

(I)

wherein

G is a residue of an optionally alkoxylated polyhydroxy compound;

m, n and p are numbers and m+n+p is from 2 to 10;

m and n are independently an number from 1 to 8;

p is from 0 to 8;

x is an integer number from 0 to 10, and when x is 0 A is directly linked to the carbonyl group;

A represents, each independently, CHR$_3$, O, S, NR$_4$ where R$_4$ is an alkyl C$_1$-C$_6$ group;

Y represents, each independently a direct bond or a substituted or unsubstituted divalent linking group comprising 1 to 14 carbon atoms;

Z represents, each independently, a radically polymerizable functional group selected from the group consisting of an acrylate, a methacrylate, a styrene, an acryl amide, a maleate, a fumarate, an itaconate, a vinyl ether, an allyl ether, an allyl ester, a maleimide, a vinyl nitrile and a vinyl ester;

R$_3$ represents, each independently hydrogen, alkyl C$_1$-C$_{12}$, substituted or unsubstituted phenyl, aryl or heteroaryl, cycloalkyl C$_5$-C$_6$, alkyl C$_1$-C$_{12}$ which is substituted with SH, —N(alkyl C$_1$-C$_6$)$_2$, piperidino, morpholino, piperazino, —OH, —O(alkyl C$_1$-C$_{12}$), —COOH; or C$_1$-C$_{12}$ alkoxy;

R$_1$, R$_2$ are, each independently, hydrogen, alkyl C$_1$-C$_{12}$, substituted or unsubstituted phenyl, substituted or unsubstituted aryl, substituted or unsubstituted heteroaryl, cycloalkyl C$_5$-C$_6$, alkyl C$_1$-C$_{12}$ which is substituted with SH, —N(alkyl C$_1$-C$_6$)$_2$, piperidino, morpholino, piperazino, —OH, —O(alkyl C$_1$-C$_{12}$), —COOH; or C$_1$-C$_{12}$ alkoxy.

2. The compound of Formula (I) according to claim 1, wherein m+n+p is has a value ranging from 2 to 8.

3. The compound of Formula (I) according to claim 1, wherein m has a value ranging from 1 to 6.

4. The compound of Formula (I) according to claim 1, wherein n has a value ranging from 1 to 6.

5. The compound of Formula (I) according to claim 1, wherein x has a value ranging from 0 to 10.

6. The compound of Formula (I) according to claim 1, wherein x has a value ranging from 0 to 6.

7. The compound of Formula (I) according to claim 1, wherein A is CHR$_3$.

8. The compound of Formula (I) according to claim 1, wherein G is chosen among monomeric and oligomeric polyols comprising ethoxylated and/or propoxylated moieties and mixtures thereof.

9. The compound of Formula (I) according to claim 1, wherein R$_1$ and R$_2$ are both a methyl group.

10. The compound of Formula (I) according to claim 1, wherein R$_3$ is hydrogen.

11. A ultra violet light or blue light photopolymerizable composition or an ultra violet or blue light photopolymerizable ink or coating which comprises at least one compound of Formula (I) as defined in claim 1, optionally in combination with at least one co-initiator.

12. A process for photopolymerizing compositions and photopolymerizable inks or coatings, which comprises the following steps:

I. preparing a photopolymerizable composition comprising:
   a. 50 to 99.9% by weight of at least one unsaturated ethylenic compound;
   b. 0.1 to 35% by weight of at least a compound of Formula (I), as specified in claim 1, and II. photopolymerizing the composition of step (I) with a light source.

13. The process of claim 12, wherein the photopolymerization is carried out with a LED light source emitting at wavelengths from 365 nm to 420 nm.

14. The process of claim 12, further comprising the step of applying said photopolymerizable composition to a substrate prior to photopolymerizing it.

15. The process of claim 12, wherein at least one co-initiator is also present in said photopolymerizing compositions.

16. An article of manufacture prepared according to the process of claim 12.

* * * * *